(12) United States Patent
Shuber

(10) Patent No.: US 6,844,155 B2
(45) Date of Patent: Jan. 18, 2005

(54) METHODS FOR DETECTING CONTAMINATION IN MOLECULAR DIAGNOSTICS USING PCR

(75) Inventor: Anthony P. Shuber, Milford, MA (US)

(73) Assignee: Exact Sciences Corporation, Marlborough, MA (US)

( * ) Notice: Subject to any disclaimer, the term of this patent is extended or adjusted under 35 U.S.C. 154(b) by 0 days.

(21) Appl. No.: 09/870,729

(22) Filed: May 30, 2001

(65) Prior Publication Data

US 2002/0025525 A1 Feb. 28, 2002

Related U.S. Application Data

(63) Continuation of application No. 09/177,243, filed on Oct. 22, 1998, now abandoned.
(60) Provisional application No. 60/063,219, filed on Oct. 23, 1997.

(51) Int. Cl.[7] .......................... C12Q 1/68; C12P 19/34; C12N 5/00
(52) U.S. Cl. .................. 435/6; 435/91.2; 435/91.1; 435/91.51; 536/25.32
(58) Field of Search .................. 435/6, 91.2, 91.1, 435/91.51; 536/25.32

(56) References Cited

U.S. PATENT DOCUMENTS 4,965,188 A * 10/1990 Mullis et al. .................. 435/6
5,882,856 A    3/1999 Shuber .......................... 435/6
6,518,026 B2 *  2/2003 Hartley ......................... 435/6

FOREIGN PATENT DOCUMENTS

| EP | 0 415 755 A2 | 3/1991 | ............ C12Q/1/68 |
| WO | 91/15601 | * 10/1991 | |
| WO | WO 91/15601 | 10/1991 | ............ C12Q/1/68 |
| WO | WO 91/17270 | 11/1991 | ............ C12Q/1/68 |

OTHER PUBLICATIONS

Shuber et al., "A Simplified Procedure for Developing Multiplex PCRs," *Genome Research*, vol. 5 (1995), pp. 488–493.

Weighardt et al., "A Simple Procedure for Enhancing PCR Specificity," *PCR Methods and Applications*, vol. 3, No. 1 (Aug. 1993), pp. 77–81.

* cited by examiner

*Primary Examiner*—Kenneth R. Horlick
*Assistant Examiner*—Joyce Tung
(74) *Attorney, Agent, or Firm*—Mintz, Levin, Cohn, Ferris, Glovsky and Popeo, P.C.; Ivor R. Elrifi, Esq.; Naomi S. Biswas, Esq.

(57) ABSTRACT

The invention provides methods for detecting contamination in a PCR reaction. Methods of the invention are especially useful for detection of contamination in heterogeneous samples containing a rare nucleic acid to be detected.

12 Claims, 5 Drawing Sheets

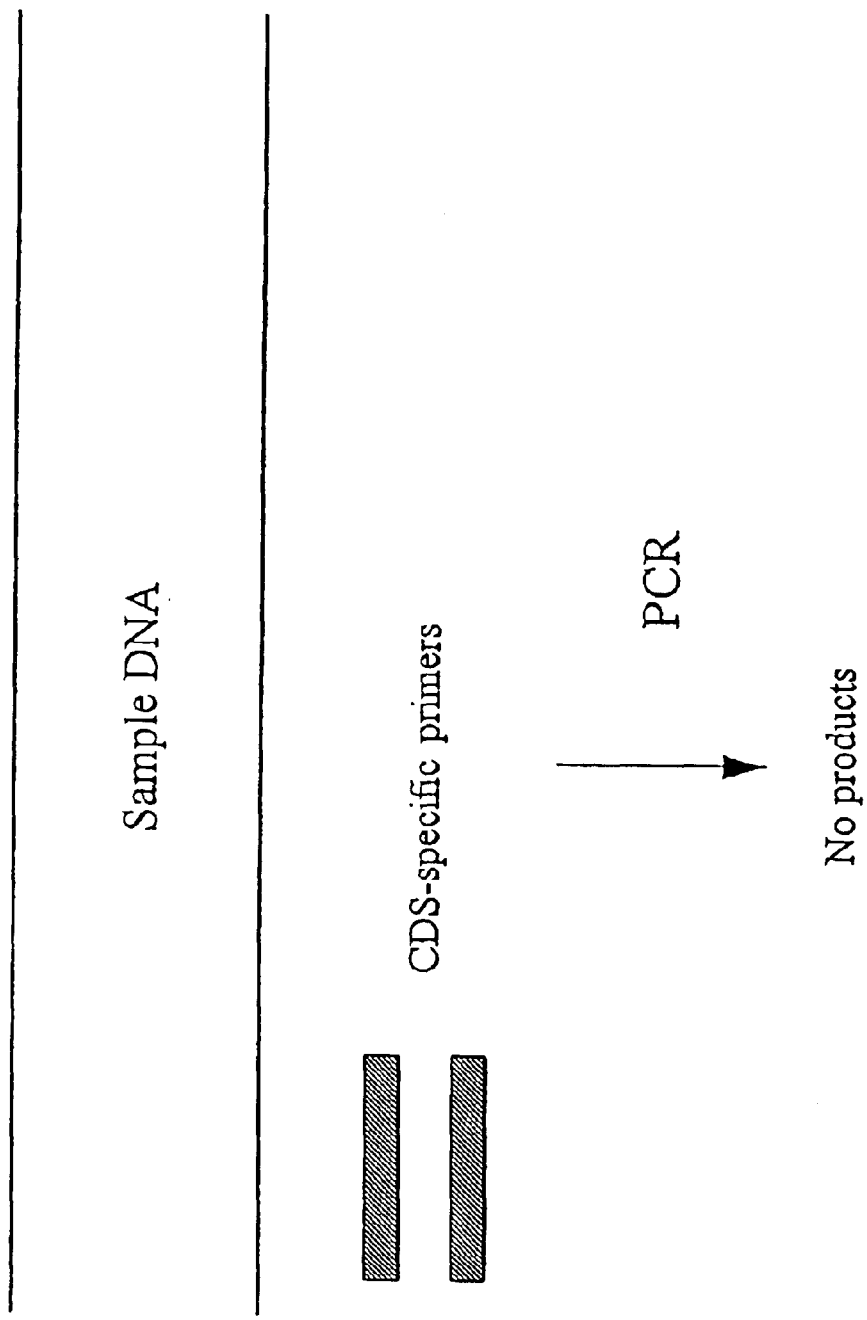

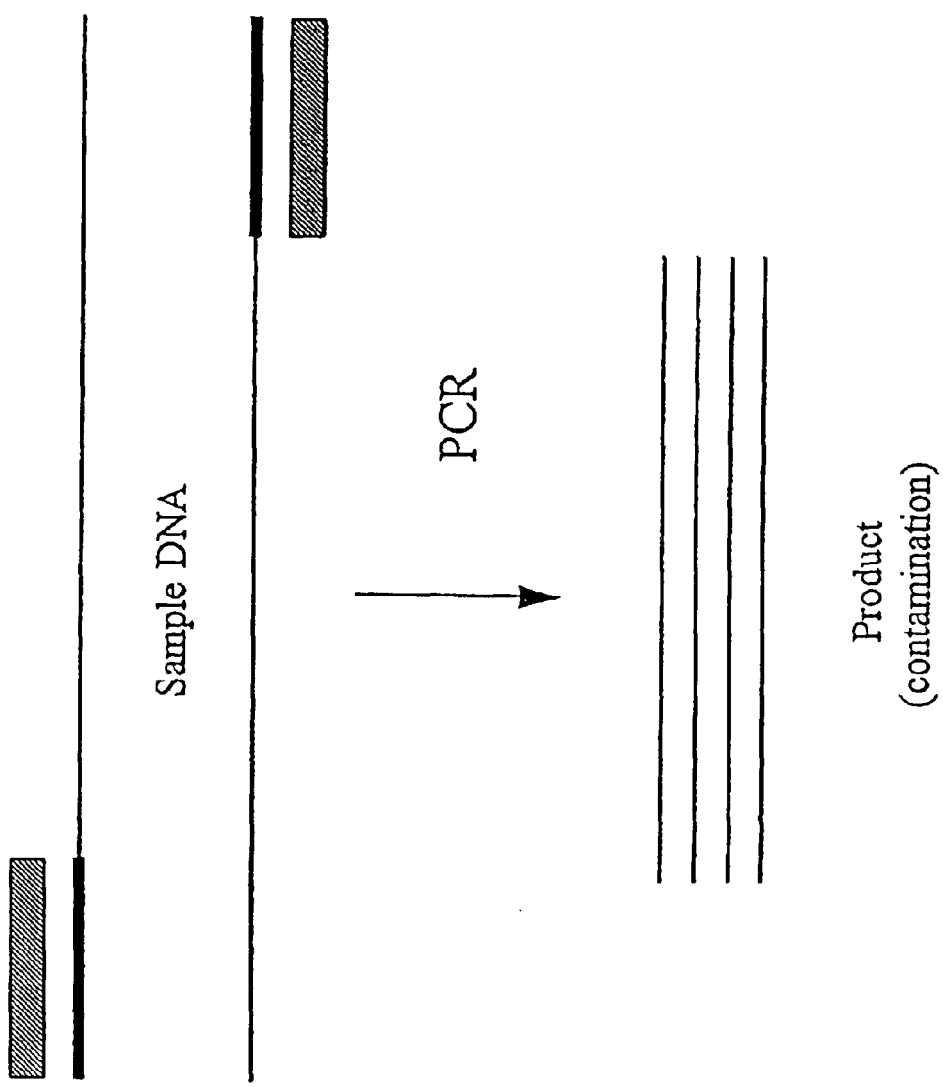

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 1
gcggtcccaa aagggtcagt                                               20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 2
gattcctaca ggaagcaagt agtaattg                                      28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 3
taatggtgaa tatcttcaaa tgatttag                                      28

METHODS FOR DETECTING CONTAMINATION IN MOLECULAR DIAGNOSTICS USING PCR

This application is a continuation of U.S. patent application Ser. No. 09/177,243, filed Oct. 22, 1998 abandoned, which claims the benefit of the filing date of provisional application Ser. No. 60/063,219, filed Oct. 23, 1997, the entire disclosures of both applications are incorporated herein by reference.

BACKGROUND OF THE INVENTION

The polymerase chain reaction (PCR) is a widely-used clinical laboratory procedure for sequence-specific target amplification. However, contamination is an ongoing problem. For many PCR applications, it is essential that the only DNA that enters the reaction is the template to be amplified.

Increases in the sensitivity and specificity of PCR have enabled analysis of heterogeneous DNA (e.g., from tumor biopsies, stool). The DNA to be amplified is typically a rare event in the context of a heterogeneous sample. However, as the degree of sample heterogeneity increases, the tolerable threshold of background (signal generated from a negative control sample) becomes increasingly lower. This is necessary to retain a sufficient signal to noise ratio between positive clinical samples and negative control samples within an assay, and therefore to retain high confidence in the assay results. The end result of applying PCR to more heterogeneous DNA environments is a reduced tolerance for pre-PCR contamination from previous amplified material. Currently, there are three methods applied to prevent PCR contamination: (1) physical separation of the sample, pre-PCR setup, and post-PCR manipulations; (2) use of Uracil DNA-glycosylase and dUTP instead of dTTP, and (3) the use of UV irradiation.

Thousands of samples may be analyzed in a single clinical assay with multiple PCR negative controls added. In this context, an investigator relies on the presence or absence of amplified product within a limited number of negative control samples to confirm the origin of amplification products observed in experimental samples. If only one PCR negative control sample is positive, the entire assay is invalid, and must be repeated. In an assay containing 1000 samples, each sample must be run with another set of negative controls when contamination is observed.

However, the mere lack of amplification product within the PCR negative control is not determinative of a positive PCR result in a sample in which contamination is rare. This kind of sporadic contamination is especially problematic in an extremely large throughput assay in which 5 to 10 negative controls are run for approximately every 1000 samples. Statistically, the likelihood of sporadic contamination in, for example, 1000 samples will not be detected in only 5 negative controls. Sporadic contamination is also a significant problem when PCR based analyses are performed on heterogeneous (rare event analysis) samples in which a positive result is generated from, for example, 1–5% of the total amplification product present within the sample. Generally, within a PCR based inherited disease diagnostic assay, given the 50% heterogeneity that exists in any genomic DNA sample, a 1–5% increase in signal in a true negative sample would appear as a slight increase in background, but would not indicate a false positive result. However, within an assay involving samples with heterogeneous populations of DNA, a 1–5% positive signal generated by a true negative sample would result in a false positive.

In addition, even within an inherited disease diagnostic assay, if there were 1000 samples analyzed and 5–10 negative control PCR reactions were run in parallel, and one or two of the negative control samples were positive, results from any of the samples themselves would be compromised. If the contamination of the PCR negative control samples is truly sporadic, then repeat analysis of all 1000 samples is probably not necessary and extremely costly. The lack of amplification product within the PCR negative control samples is not determinative that a positive PCR result within an experimental sample set is not from rare (sporadic) contamination that has occurred in only a few samples within the assay (and not due to the negative controls run in parallel).

In many assays, "normal" PCR contaminants (e.g., resulting from purification problems) are an even greater hindrance and leads to decreased sensitivity of the assay. These "normal" PCR contaminants can lead to false negative results that undermine the accuracy of (and confidence in) the particular assay.

Therefore, methods are needed for performing clinical analyses on samples of DNA heterogeneity (e.g. sporadic cancer detection) such that sporadic contamination from previous amplification product or "normal" PCR contaminants do not result in false positive or false negative results.

SUMMARY OF THE INVENTION

The invention provides methods for determining whether contamination from previous amplification product exists in products of a polymerase chain reaction (PCR). Specifically, the invention relates to methods for detecting the presence of PCR products (amplicons) that would not be present but for contamination from previous amplification product in the PCR sample. Methods of the invention are useful for detection of contamination in any PCR. Furthermore, the methods of the invention are useful to avoid false negative and false positive results and the decreased assay sensitivity associated with PCR contamination. However, such methods are especially useful in heterogeneous samples, particularly samples in which the detection of a rare event (i.e. a small subpopulation of a nucleic acid in a heterogeneous sample) is the ultimate object of the PCR.

In a preferred embodiment, methods of the invention comprise the utilization of optimal primer construction for PCR. Accordingly, in a highly-preferred embodiment, methods of the invention comprise conducting a first amplification using one or more (preferably two) chimeric primers. A chimeric primer, for purposes of the invention, is one comprising a primer having substantial sequence specificity with the template to be amplified (a template-specific sequence) and a 5' end that is referred to herein as a "contamination detection sequence" (CDS). Methods further comprise conducting a second, parallel, amplification reaction using at least one (preferably two) contamination detection sequence (without the attached template-specific sequence, or with only a minimal number of template-specific bases, as described below) as a primer. Finally, detection of an amplicon in the second amplification reaction means that the sample is contaminated with previous amplification product, because no such amplicon would be generated absent contamination.

A contamination detection sequence may be any sequence (regardless of length) that does not have substantial sequence specificity (i.e., does not hybridize under stringent conditions) with the template. See FIG. 2A. Accordingly, methods of the invention comprise conducting two amplification reactions on each sample suspected to contain a template sequence, the amplification of which is desired. The first reaction utilizes the chimeric primers described above, and yields the desired amplicon (which may then be sequenced, probed, etc.). The second amplification reaction utilizes only the contamination detection sequence as primers (which are non-specific relative to the template). Any amplicon produced in the second reaction is evidence of contamination with previous amplification product.

In a preferred embodiment, the amplification reaction is selected from PCR, reverse transcriptase PCR, and quantitative PCR. Also in a preferred embodiment, the sample containing nucleic acid to be amplified is a stool sample. A stool sample contains a highly-heterogeneous population of nucleic acids. Human nucleic acids represent a small portion of the nucleic acid present in stool. More specifically, a stool sample may contain molecular indicia of cancer, specifically colorectal cancer, that occurs as a small subpopulation (typically on the order of about 1% at early stages of cancer or precancer) of the total nucleic acid in the stool. Sensitive assays (which may or may not involve amplification) have been developed to detect such small subpopulations. See, e.g., U.S. Pat. No. 5,670,325, incorporated by reference herein. Amplification of a nucleic acid containing a mutation indicative of cancer or precancer may be confounded by PCR contaminants in the sample, especially if the detection limits of the assay are near or above the percent contaminants in the sample. The present invention detects PCR contaminants, thus allowing a given PCR reaction to be excluded from analysis on a sample-by-sample basis. Thus, if four separate samples are taken for amplification, each sample is divided into two subsample aliquots, one of which is amplified using chimeric primers, and in the other, the contamination detection sequence primers are used to check for contamination in the aliquot. Therefore, each aliquot of sample for which amplification is sought has its own quality control assay.

These and other advantages and aspects of the invention will be understood upon consideration of the following detailed description thereof.

BRIEF DESCRIPTION OF THE DRAWINGS

FIG. 2B shows a schematic representation of PCR amplification using CDS-specific primers on uncontaminated sample (resulting in no amplified product).

FIG. 2C shows a schematic representation of PCR amplification using CDS-specific primers on contaminated sample (resulting in amplified product).

DETAILED DESCRIPTION OF THE INVENTION

Methods of the invention comprise optimal PCR primer design. Normally, target-specific PCR primers are complementary to sequences present within the target. The target sequence is part of, and endogenous to, the target DNA analyte (the analyte can be any target DNA of interest: human DNA, viral DNA etc.) and is therefore one that is expected to be present in all of the experimental samples (in the case of inherited disease diagnostics), or at least in all of the positive samples (in the case of infectious disease diagnostics).

Figure 1:
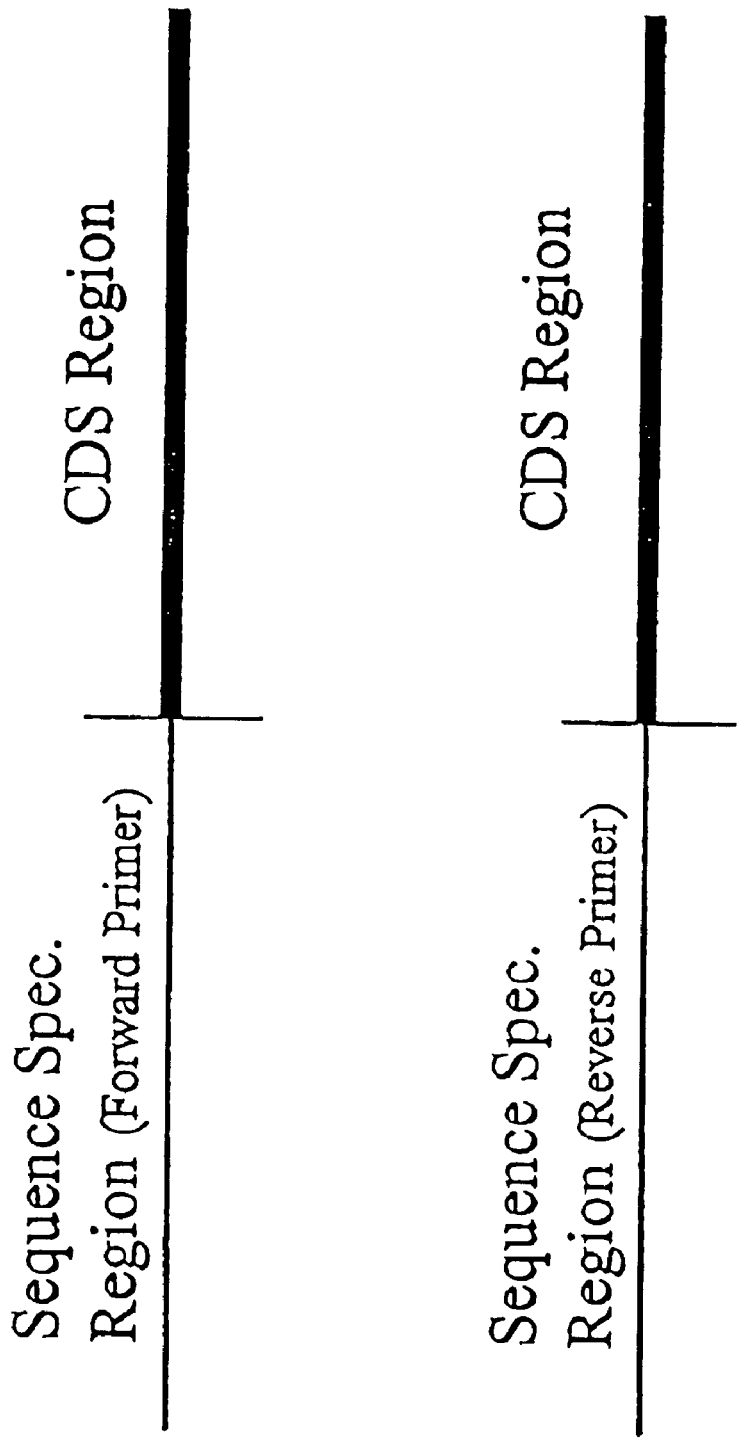
FIG. 1 shows a schematic diagram of the chimeric primers used in the present invention.
Figure 2A:
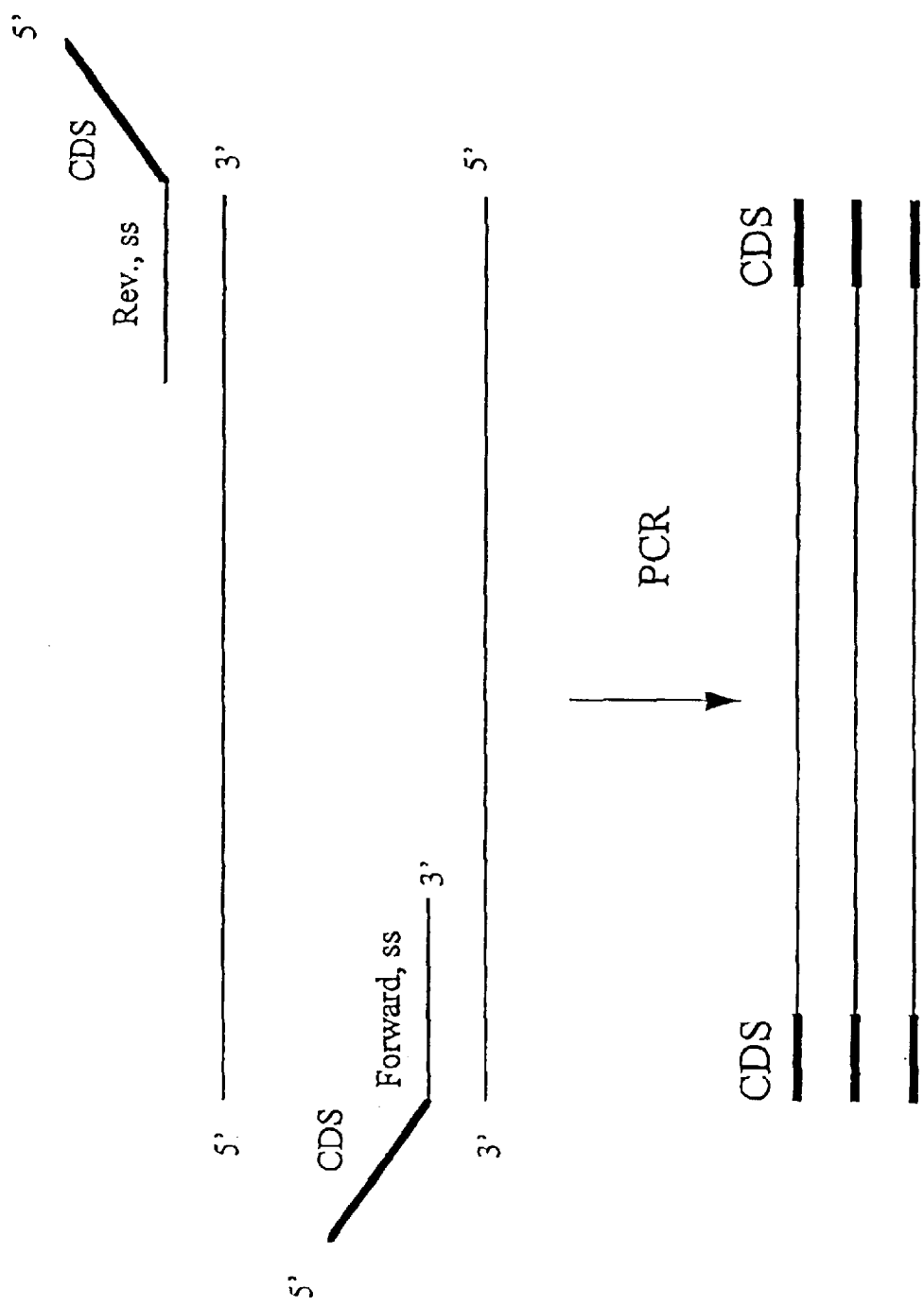
FIG. 2A shows a schematic representation of PCR amplification using chimeric primers.
Figure 3:
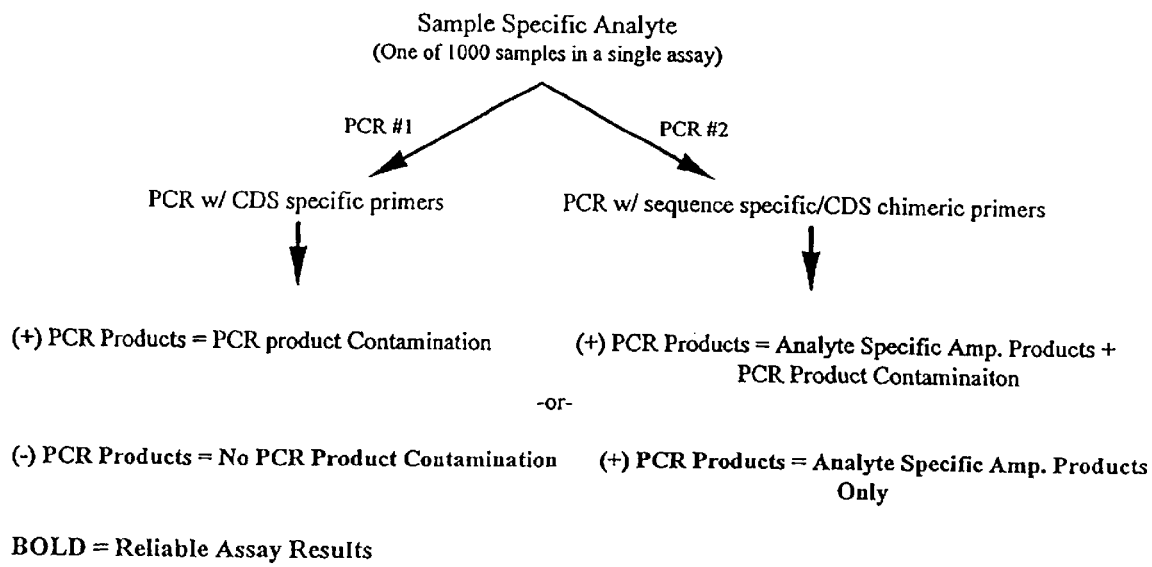
FIG. 3 shows a schematic diagram of an assay performed using the methods of the invention.

Methods of the invention comprise PCR primers that have a non-homologous or non-complementary "contamination detection sequence" ("CDS") attached to the 5' end of target-specific PCR primers. (See FIG. 1). The CDS region is neither homologous to, nor complementary to, any endogenase (template) sequence. Therefore, following any PCR involving chimeric primers, the CDS becomes incorporated into the PCR products (amplicons) generated from the PCR. (See FIG. 2A). Therefore, only PCR products from previous reactions have the CDS region contained within them.

In the present invention, a sample to be assayed for a particular analyte (which may be one of hundreds or thousands in a single clinical assay) is analyzed by two distinct, parallel amplification reactions. In a first reaction, PCR is performed on the sample using chimeric sequences that contain a template-specific sequence (a sequence substantially complementary to a specific DNA analyte) and a 5' CDS sequence (the CDS sequence is contiguous to the 5' end of the template specific sequence). In a second reaction, PCR is performed on the sample using primers that are specific for previously amplified amplicons containing the CDS sequence. The CDS primers (1) may be sequences that are specific for the CDS sequence alone (i.e., with no cross-reactivity to the target analyte sequence), or (2) the primers can comprise the CDS sequence with additional bases attached to the 3' end. From one to nine bases may be added at the 3' end of the CDS sequence and may serve to provide additional specificity. The CDS primers will not effectively prime the target analyte sequence.

The presence of amplified product (or amplicon) as a result of the PCR using the chimeric primer indicates a positive result for the presence of the particular analyte, but may also reflect contamination from previous PCR product.

The PCR with CDS-specific primers acts as negative control. Because the only samples that contain the CDS sequence will be those generated by previous PCR events within the lab, the presence of amplified product after PCR with the CDS-specific primers indicates that that particular sample is contaminated, and the results should be discarded. The lack of amplified product reflects the absence of PCR-based contaminants in a particular sample as portion of a sample.

Accordingly, the present invention eliminates the degree of repeat sample analyses performed within, for example, high throughput assays by specifically identifying only samples that have contamination.

The invention also provides additional protection needed within assays of heterogeneous samples, where sporadic contamination is more likely to be the source of contamination. It enables identification of the specific samples within the assays that are truly contaminated. The invention also provides a sample specific internal control for determining PCR product contamination.

The present invention is suitable for use with a variety of experimental samples that may contain a particular DNA analyte. Biological samples may be used in the present invention, including blood and stool samples.

The methods of the present invention are especially suitable for applications such as inherited disease diagnostics and related kits; infectious disease diagnostics and related kits; clinical assays involving sporadic cancer detection (e.g. testing DNA from stool for colorectal cancer) and related kits; and other "rare event" clinical assay and related kits.

EXAMPLE 1

Stool sample is collected and prepared as described in U.S. Pat. No. 5,741,650 and in copending applications Ser.

No. 08/876,638, filed Jun. 16, 1997, both incorporated by reference herein. Specifically, stool is collected and prepared so that a sample contains at least a cross-sectional portion of a stool voided by a patient. Alternatively, whole stool may be used. The sample is homogenized in a physiologically compatible buffer (e.g., having a final concentration: 500 mM Tris, 16 mM EDTA and 10 mM NaCl, pH 9.0), using an Exactor II shaker for 15 minutes. A 20% SDS solution is added to a final concentration of 0.5%. Proteinase K is also added to a final concentration of 500 µg/ml and incubated at 37° C.

For exemplification, sequence-specific primers suitable for PCR are chosen to correspond to a portion of the kras gene sequence. These are: Primer 1 (SEQ. ID. NO. 2): 5'-GATTCCTACA GGAAGCAAGTAGTAATTG-3', and Primer 2 (SEQ. ID. NO. 3): 5'-TAATGGTGAATATCT TCAAATGATTTAG-3'.

The contamination detection sequence (CDS) is 5'-GCGGTCCCAAAAGGGTCAGT-3' (SEQ. ID. NO. 1). The chimeric primers contain the 20-nucleotide CDS sequence attached (i.e. contiguous) to the 5' end of the individual sequence-specific primers (primer 1 or primer 2). Oligonucleotides are HPLC purified and quantitated by spectrophotometry.

PCR amplifications are performed using from about 4 µl (1–2 µg) to about 10 µl (5–50 ng) of genomic DNA prepared from stool samples. PCR amplifications are done using a Perkin-Elmer 9600 Thermal Cycler (Perkin-Elmer, Norwalk, Conn.) for 28 cycles with ramping (94° C./10-sec hold with 48-sec ramp, 60° C./10-sec hold with 36-sec ramp, 72° C./10-sec hold with 38 sec ramp). Reactions (50 µl) are carried out in 1× PCR buffer (10 mM Tris-HCl at pH 8.3, 50 mM Kcl, 1.5 mM $MgCL_2$), 200 µm dNTPs, 2.5 units, of Taq polymerase (Perkin-Elmer, Norwalk, Conn.).

For PCR product analyses, 8 µl of the amplification reactions is loaded directly onto a 2% ethidium bromide stained agarose gel and electrophoresed at 250 V for 90 min. The amplification products are visualized with a UV transilluminator (Fotodyne, New Berlin, Wis.) and photographed with an Alpha Innotech IS-500 Digital Imaging System version 1.97 (Sun Bioscience Inc., Branford, Conn.).

A first PCR is performed in a first aliquot of stool sample (containing kras) using chimeric primers, wherein the forward primer comprises primer 1 with the CDS contiguous with its 5' end; and the reverse primer comprises primer 2 with the CDS contiguous with its 5' end. The first PCR results in an amplicon comprising both chimeric primers and the intervening template sequence.

A second PCR is performed on a second aliquot of stool sample in which both the forward and reverse primers are the CDS. If contamination from previous PCR cycles is present in the sample, the second PCR will product an amplicon. If no contamination is present in the sample, no amplicon is observed in the second aliquot.

What is claimed is:

1. A method for detecting cross-sample contamination in an amplification reaction, said method comprising the steps of:

conducting an amplification reaction in a first nucleic acid sample, using at least one chimeric primer comprising a first portion that hybridizes with at least a portion of a target nucleic acid, the amplification of which is desired, and a second, contamination detection portion that does not hybridize with said target nucleic acid;

conducting a subsequent control amplification reaction in a second nucleic acid sample, using at least one primer to amplify specifically said contamination detection portion of said chimeric primer; and determining whether said second sample has been contaminated by an amplicon from said first sample by determining whether said control reaction produces an amplicon.

2. The method of claim 1, wherein said second portion is 5' to said first portion in each of said at least one chimeric primers.

3. The method of claim 1, wherein said at least one primer in said control reaction is not complementary to any contiguous nucleic acid sequence in any target nucleic acid in said second sample.

4. The method of claim 1, wherein said at least one primer used in said control reaction is substantially complementary to said contamination detection portion.

5. The method of claim 1, wherein said at least one primer used in said control reaction is substantially identical to said contamination detection portion.

6. The method of claim 1, wherein at least one of said amplification reactions is selected from the group consisting of PCR, quantitative PCR, and reverse-transcriptase PCR.

7. The method of claim 1, wherein said samples comprise a heterogeneous population of nucleic acids.

8. The method of claim 7, wherein said samples comprise a stool sample.

9. The method of claim 7, wherein said samples comprise a blood sample.

10. The method of claim 1, wherein said contamination detection portion is about 20 nucleotides.

11. The method of claim 1, wherein said nucleic acid comprises DNA.

12. The method of claim 1, wherein said determination step comprises using a sequence-specific nucleic acid probe to capture said amplicon from said first sample.

* * * * *